(12) United States Patent
Thramann et al.

(10) Patent No.: US 8,652,181 B2
(45) Date of Patent: Feb. 18, 2014

(54) CERVICAL PLATE

(75) Inventors: Jeffery Thramann, Longmont, CO (US); Michael Fulton, Superior, CO (US)

(73) Assignee: Lanx, Inc., Broomfield, CO (US)

( * ) Notice: Subject to any disclaimer, the term of this patent is extended or adjusted under 35 U.S.C. 154(b) by 1151 days.

(21) Appl. No.: 11/456,056

(22) Filed: Jul. 6, 2006

(65) Prior Publication Data
US 2007/0016206 A1 Jan. 18, 2007

Related U.S. Application Data

(63) Continuation-in-part of application No. 10/932,272, filed on Sep. 1, 2004, now Pat. No. 7,175,623, which is a continuation-in-part of application No. 10/632,760, filed on Aug. 1, 2003, now Pat. No. 7,077,843, which is a continuation-in-part of application No. 10/178,371, filed on Jun. 24, 2002, now Pat. No. 6,602,257.

(51) Int. Cl.
*A61B 17/80* (2006.01)

(52) U.S. Cl.
USPC .......................................... 606/289; 606/287

(58) Field of Classification Search
USPC ........... 606/76, 268, 269, 270, 280, 285, 289, 606/290, 291; 411/82, 82.2, 82.3, 95, 411/111–113, 119–121, 171, 183–185, 197, 411/201, 212, 220, 225, 258, 259, 368, 369, 411/371.1, 446, 451.1–455, 508–510, 533, 411/541, 542, 924.1, 929, 930, 963
See application file for complete search history.

(56) References Cited

U.S. PATENT DOCUMENTS

| | | | |
|---|---|---|---|
| 2,409,638 A | 10/1946 | Lyon | |
| 2,942,640 A * | 6/1960 | Lundeberg | 411/302 |
| 3,061,455 A * | 10/1962 | Anthony | 411/258 |
| 3,093,177 A * | 6/1963 | Villo | 411/302 |
| 3,263,726 A * | 8/1966 | McKay | 411/304 |
| 3,486,505 A | 12/1969 | Morrison | |
| 3,498,352 A * | 3/1970 | Duffy | 411/302 |
| 3,552,467 A * | 1/1971 | Bergere | 411/301 |
| 3,711,347 A * | 1/1973 | Wagner et al. | 156/91 |
| 3,737,355 A * | 6/1973 | Epstein et al. | 156/293 |
| 3,750,652 A | 8/1973 | Sherwin | |
| 3,770,036 A * | 11/1973 | Sherman | 411/508 |

(Continued)

FOREIGN PATENT DOCUMENTS

FR 2778088 A1 11/1999
WO 99/56653 11/1999

OTHER PUBLICATIONS

Miyajima, Masami "Digital Image Reading Apparatus" Publication No. US-2002/0015189; Published on Feb. 7, 2002.

(Continued)

*Primary Examiner* — Pedro Philogene
*Assistant Examiner* — Lynnsy Schneider
(74) *Attorney, Agent, or Firm* — Perkins Coie LLP

(57) ABSTRACT

Screw back out prevention devices to inhibit screws from reverse threading or backing out are provided. The devices include first bonding materials on either a bushing in a bore of a plate or directly on the bore and second bonding materials on the screw head. The bonding materials for a bond that inhibits back out or reverse threading of the screw.

7 Claims, 8 Drawing Sheets

(56) References Cited

U.S. PATENT DOCUMENTS

| | | | |
|---|---|---|---|
| 3,784,435 A * | 1/1974 | Bagheri et al. | 156/293 |
| 3,834,021 A | 9/1974 | White et al. | |
| 3,835,615 A * | 9/1974 | King, Jr. | 403/408.1 |
| 3,975,787 A * | 8/1976 | Newnom | 470/19 |
| 4,033,393 A * | 7/1977 | Bedi | 411/301 |
| 4,164,971 A * | 8/1979 | Strand | 411/301 |
| 4,282,913 A * | 8/1981 | Trimmer | 411/303 |
| 4,310,273 A * | 1/1982 | Kirrish | 411/338 |
| 4,659,268 A * | 4/1987 | Del Mundo et al. | 411/34 |
| 4,701,088 A * | 10/1987 | Crull | 411/369 |
| 4,794,918 A | 1/1989 | Wolter | |
| 5,085,660 A | 2/1992 | Lin | |
| 5,122,020 A * | 6/1992 | Bedi | 411/302 |
| 5,221,170 A * | 6/1993 | Duffy et al. | 411/428 |
| 5,281,065 A * | 1/1994 | Wu | 411/258 |
| 5,332,360 A * | 7/1994 | Correia et al. | 415/209.3 |
| 5,364,399 A | 11/1994 | Lowery et al. | |
| 5,391,031 A * | 2/1995 | Medal | 411/82.5 |
| 5,407,312 A | 4/1995 | Terrizzi | |
| 5,494,391 A * | 2/1996 | Zhou | 411/369 |
| 5,558,674 A | 9/1996 | Heggeness et al. | |
| 5,578,034 A | 11/1996 | Estes | |
| 5,607,428 A * | 3/1997 | Lin | 606/287 |
| 5,672,036 A * | 9/1997 | Medal | 411/82 |
| 5,676,666 A | 10/1997 | Oxland et al. | |
| 5,697,744 A * | 12/1997 | Medal | 411/82 |
| 5,725,345 A * | 3/1998 | Zhov | 411/369 |
| 5,735,853 A * | 4/1998 | Olerud | 606/71 |
| 5,741,258 A | 4/1998 | Klaue et al. | |
| 5,782,830 A | 7/1998 | Farris | |
| 5,885,299 A | 3/1999 | Winslow et al. | |
| 5,902,303 A * | 5/1999 | Eckhof et al. | 606/60 |
| 5,904,683 A | 5/1999 | Pohndorf et al. | |
| 5,951,558 A | 9/1999 | Fiz | |
| 5,954,722 A * | 9/1999 | Bono | 606/281 |
| 5,957,927 A | 9/1999 | Magee et al. | |
| 6,129,730 A | 10/2000 | Bono et al. | |
| 6,139,550 A | 10/2000 | Michelson | |
| 6,152,927 A | 11/2000 | Farris et al. | |
| 6,159,213 A | 12/2000 | Rogozinski | |
| 6,193,721 B1 | 2/2001 | Michelson | |
| 6,224,599 B1 | 5/2001 | Baynham et al. | |
| 6,224,602 B1 | 5/2001 | Hayes | |
| 6,235,033 B1 * | 5/2001 | Brace et al. | 606/288 |
| 6,235,034 B1 | 5/2001 | Bray | |
| 6,258,089 B1 | 7/2001 | Campbell et al. | |
| 6,261,291 B1 | 7/2001 | Talaber et al. | |
| 6,261,296 B1 | 7/2001 | Aebi et al. | |
| 6,306,139 B1 | 10/2001 | Fuentes | |
| 6,331,179 B1 * | 12/2001 | Freid et al. | 606/279 |
| 6,413,259 B1 | 7/2002 | Lyons et al. | |
| 6,436,101 B1 | 8/2002 | Hamada | |
| 6,454,769 B2 * | 9/2002 | Wagner et al. | 606/279 |
| 6,503,250 B2 | 1/2003 | Paul | |
| 6,533,786 B1 | 3/2003 | Needham et al. | |
| 6,540,748 B2 | 4/2003 | Lombardo | |
| 6,565,303 B1 | 5/2003 | Riccitelli et al. | |
| 6,575,975 B2 * | 6/2003 | Brace et al. | 606/86 B |
| 6,605,090 B1 * | 8/2003 | Trieu et al. | 606/281 |
| 6,626,907 B2 | 9/2003 | Campbell et al. | |
| 6,695,846 B2 | 2/2004 | Richelsoph et al. | |
| 7,172,593 B2 | 2/2007 | Trieu et al. | |
| 7,229,443 B2 * | 6/2007 | Eberlein et al. | 606/86 A |
| 7,686,837 B2 * | 3/2010 | Gasser et al. | 606/287 |
| 7,771,148 B2 * | 8/2010 | Phillips | 411/82.2 |
| 2001/0001119 A1 | 5/2001 | Lombardo | |
| 2001/0021851 A1 * | 9/2001 | Eberlein et al. | 606/69 |
| 2001/0041894 A1 | 11/2001 | Campbell et al. | |
| 2002/0015189 A1 | 2/2002 | Miyajima | |
| 2002/0065517 A1 | 5/2002 | Paul | |
| 2002/0098061 A1 * | 7/2002 | Cosenza | 411/454 |
| 2002/0120273 A1 | 8/2002 | Needham et al. | |
| 2003/0040749 A1 | 2/2003 | Grabowski et al. | |
| 2003/0060828 A1 | 3/2003 | Michelson | |
| 2003/0078583 A1 | 4/2003 | Biedermann et al. | |
| 2003/0135213 A1 | 7/2003 | LeHuec et al. | |
| 2004/0030342 A1 * | 2/2004 | Trieu et al. | 606/72 |
| 2007/0212188 A1 * | 9/2007 | Wang et al. | 411/82 |
| 2008/0234753 A1 * | 9/2008 | Trieu | 606/297 |
| 2010/0249850 A1 * | 9/2010 | Cerynik et al. | 606/281 |

OTHER PUBLICATIONS

Needham, Dusty "Anterior Cervical Plating System and Method" Publication No. US-2002-0120273; Published on Aug. 29, 2002.

Grabowski, John "Bone Fixation Device" Publication No. US-2003-0040749; Published on Feb. 27, 2003.

Michelson, Gary "Dynamic Multilock Anterior Cervical Plate System Having Non-Detachably Fastened and Moveable Segments, Instrumentation, and Method for Installation Thereof" Publication No. US-2003/0060828, Published on Mar. 27, 2003.

Biedermann, Lutz "Bone Fixing Device" Publication No. US-2003/0078583. Published on Apr. 24, 2003.

Biedermann, Lutz "Bone Fixing Device" Publication No. US-2003/0078583, Published on Apr. 24, 2003.

Supplementary European Search Report, date of completion Nov. 9, 2010.

* cited by examiner

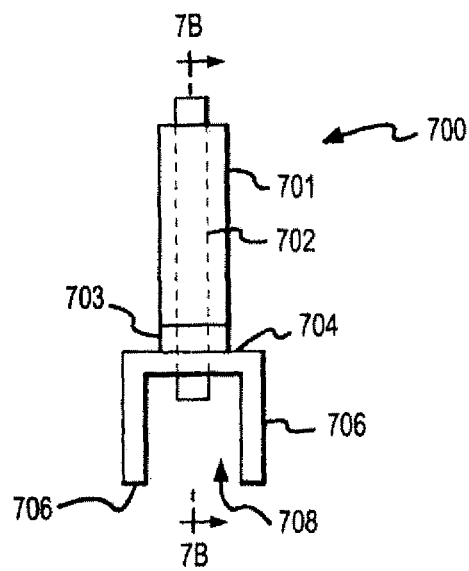 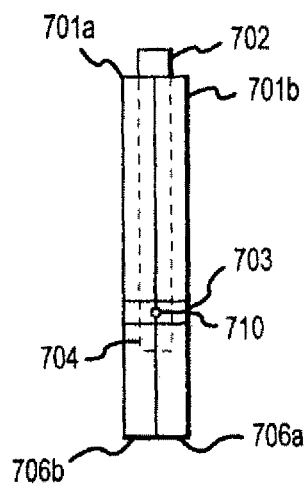
FIG.7A  FIG.7B
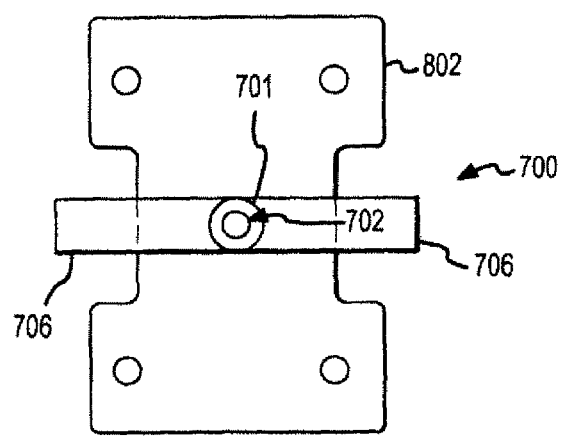
FIG.8

CERVICAL PLATE

RELATED APPLICATIONS

This application is a continuation-in-part of U.S. patent application Ser. No. 10/932,272, filed Sep. 1, 2004, titled CERVICAL PLATE WITH BACKOUT PROTECTION, now U.S. Pat. No. 7,175,623, which is a continuation-in-part of U.S. patent application Ser. No. 10/632,760, filed Aug. 1, 2003, titled CERVICAL PLATE, now U.S. Pat. No. 7,077,843, which is a continuation in part of U.S. patent application Ser. No. 10/178,371, filed Jun. 24, 2002, titled CERVICAL PLATE, now U.S. Pat. No. 6,062,257. This application also is related to U.S. patent application Ser. No. 10/178,656, filed Jun. 24, 2002, titled IMPACTOR FOR USE WITH CERVICAL PLATE.

FIELD OF THE INVENTION

The present invention relates to apparatuses and methods for treating and correcting spinal abnormalities and, more particularly, to cervical plates having backout or reverse thread protection.

BACKGROUND OF THE INVENTION

The vertebrae of the human spine are arranged in a column with one vertebra on top of the next. Between each vertebra exists an intervertebral disc that transmits force between adjacent vertebrae and provides a cushion between the adjacent vertebrae.

Sometimes, back pain is caused by degeneration or other deformity of the intervertebral disc ("diseased disc"). Conventionally, surgeons treat diseased discs by surgically removing the diseased disc and inserting a bone graft in the space vacated by the diseased disc. The adjacent vertebrae are then immobilized relative to one another. Eventually, the vertebrae grow into one solid piece of bone.

Currently, it is difficult to insert the bone graft into the vacated space and fuse the adjacent vertebrae. The current process of inserting a bone graft and fusing the adjacent vertebrae will be explained with referring to FIGS. 1 and 2. FIG. 1 shows two adjacent vertebrae 102 and 104. Located between vertebrae 102 and 104 is an intervertebral space 106 partially filled by a bone graft 108. When the bone graft 108 is first inserted into the intervertebral space 106, the adjacent vertebrae 102 and 104 are manually kept apart by the surgeon using, for example, a retracting device (not shown). As shown in FIG. 2, once the bone graft 108 is placed, the surgeon releases the adjacent vertebrae 102 and 104 allowing them to squeeze the bone graft 108 and hold the bone graft 108 in place.

To immobilize the vertebrae 102 and 104 with the bone graft 108 in place, the surgeon next applies a cervical plate 202 over the adjacent vertebrae 102 and 104. Cervical plate 202 may have a central viewing window 204 and one or more screw holes 206, in this example four screw holes 206a-206d are shown. Four bone screws (which will be identified by reference numerals 208a-208d) would be screwed into the vertebrae using the screw holes 206 to anchor the cervical plate to the vertebrae and immobilize the vertebrae with respect to one another.

As can be appreciated, attaching the cervical plate 202 using the bone screws 208 is a difficult endeavor. Generally, a temporary screw (not shown) is placed in one of the screw holes, for example 206a. Bone screw 208c would then be partially screwed into the bone at screw hole 206c. The temporary screw in hole 206a would be replaced by bone screw 208a, which would be tightened. Then the other bone screws 208 would be screwed into the bone in a cross point manner. The ability of the cervical plate to move freely in relation to the vertebrae 102 and 104 and the bone graft 108 until the bone screws anchor the plate causes difficult in attaching the cervical plate. This is made more difficult because, generally, only a portion of the cervical plate is visible to the surgeon at any given moment (due to space constraints and surgical tools).

Moreover, once threaded, bone screws 208a-d tend to backout or reverse thread. Current fusion plates have numerous backout devices, but those devices are less than satisfactory solutions in some instances. Thus, improved backout or reverse threading protection is desired.

SUMMARY OF THE INVENTION

To attain the advantages and in accordance with the purpose of the invention, as embodied and broadly described herein, apparatuses to facilitate the insertion of a bone graft into an intervertebral space and positioning of a cervical plate are provided. In particular, a cervical plate having back out prevention is provided. The plate has at least one through ole with a bushing residing in the through hole. The bushing includes a first bonding material on an inner sidewall A screw, to extend through the through hole and thread into a vertebral body, comprises a shank and head having an outer sidewall. A second bonding material resides on the outer sidewall. When the screw is threaded into a vertebral body, the first bonding material and the second bonding material substantially align and form a bond that inhibits the screw from backing out.

The foregoing and other features, utilities and advantages of the invention will be apparent from the following more particular description of a preferred embodiment of the invention as illustrated in the accompanying drawings. Further, the advantages and purpose of the invention will be realized and attained by means of the elements and combinations particularly pointed out in the appended claims.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

FIG. 7; shows an impactor illustrative of the present invention;

FIG. 8 shows the impactor of FIG. 7 with a cervical plate illustrative of the present invention;

DETAILED DESCRIPTION

Figure 1:
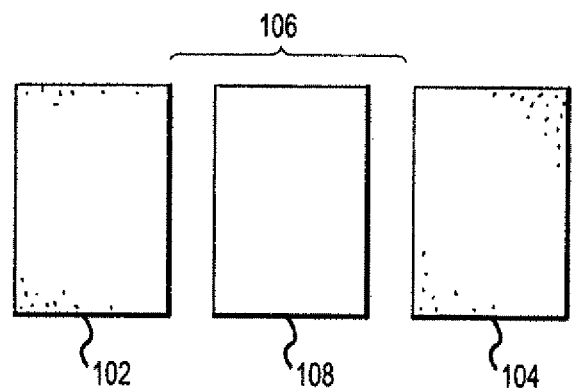
FIG. 1 shows adjacent vertebrae with a bone graft.
Figure 2:
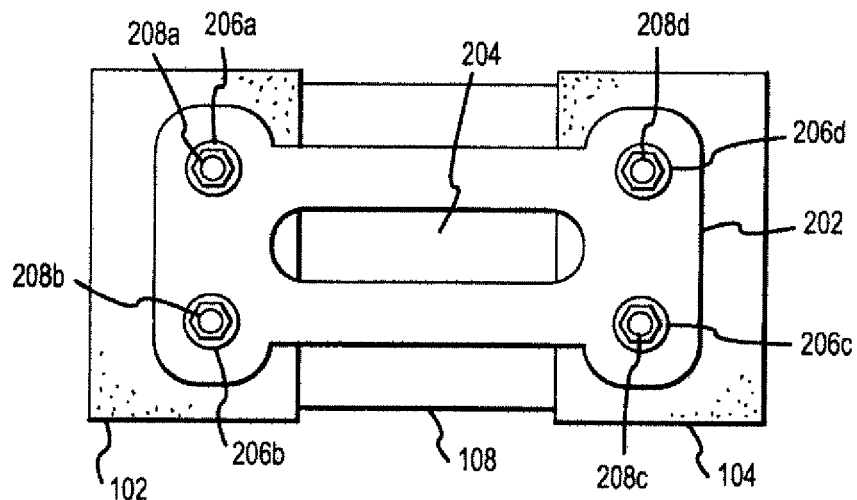
FIG. 2 shows adjacent vertebrae with a bone graft and cervical plate.
Figure 3:
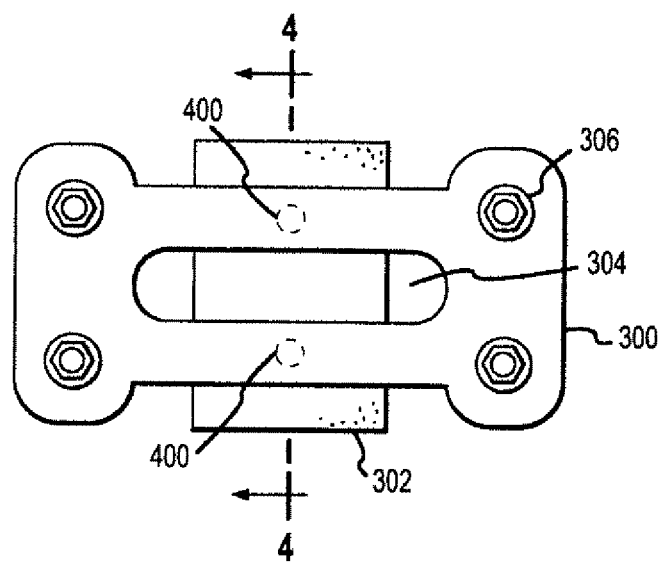
FIG. 3 shows adjacent vertebrae with a bone graft and cervical plate having an attachment mechanism illustrative of the present invention.
Figure 4:
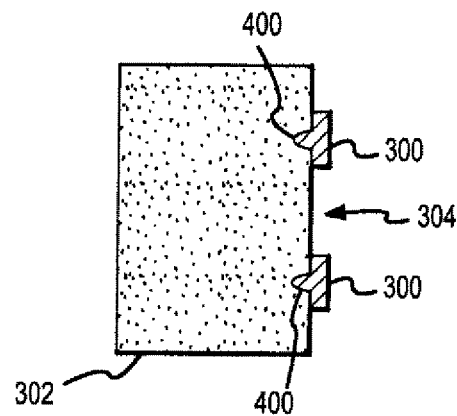
FIG. 4 shows a cross-section of the bone graft and cervical plate of FIG. 3.

Some embodiments of the present invention are described with reference to FIGS. 3 to 14. In particular, FIGS. 3 and 4 show a cervical plate 300 and bone graft 302. Cervical plate 300 has a viewing window 304, screw holes 306, and an attachment mechanism 400 (shown in phantom in FIG. 3). As best seen in FIG. 4, cervical plate 300 has attachment mechanism 400 attaching the bone graft 302 to the cervical plate 300. While cervical plate 300 could be made of numerous biocompatible materials, it is believed cervical plate 300 should be made of bio absorbable material. Bio absorbable or resorbable devises are generally known in the art, see for example, U.S. Pat. No. 6,241,771, titled RESORBABLE INTERBODY SPINAL FUSION DEVICES, issued to Gresser et al., on Jun. 5, 2001, incorporated herein by reference. Generally, the devices explained and contained herein may be constructed out or any number of biocompatible materials, including titanium, shaped memory allows, milled bone, resorbable material, PEEK, or the like.

Attachment mechanism 400 can be any of a number of different attachment mechanisms. For example, as shown in FIG. 4, attachment mechanism 400 comprises a pin or stud attached to the cervical plate inserted into a hole or detent in the bone graft 302. Alternatively, attachment mechanism 400 could be a spike inserted into bone graft 302 without bone graft 302 having a corresponding hole or detent to receive the spike, similar to a thumb tack. Alternatively, attachment mechanism 400 could comprise a pin or stud attached to the bone graft 302 inserted into a hole or detent in cervical plate 300. Also, attachment mechanism 400 could be any style snap lock or friction fitting, such as the cavity formed in FIG. 5 between protrusions 504, explained in more detail below. It would be possible to provide barbs and/or lips on attachment mechanism 400 to facilitate the connection. Moreover, while two attachment mechanisms 400 are shown, more or less attachment mechanisms could be used. Further, attachment mechanism 400 could be an adhesive layer between the cervical plate 300 and bone graft 302. Still further, attachment mechanism 400 could be a screw device so that bone graft 302 and cervical plate 300 are attached using a screw mechanism. Finally, the cervical plates 300 could be made as a single integral unit with the bone graft 302, although that would be difficult due to the numerous sizes and shapes of bone grafts and plates necessary to perform the surgery.

Figure 5:
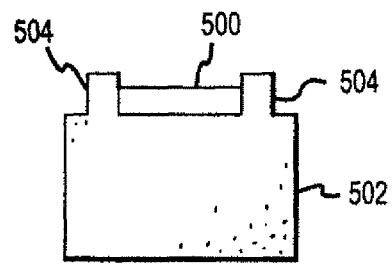
FIG. 5 shows an alternative attachment mechanism illustrative of the present invention.

FIG. 5 shows cervical plate 500 attached to a bone graft 502 by prongs 504 on bone graft 502. As shown, prongs 504 attached to the bone graft grasp cervical plate 500 forming a frictional engagement. Alternatively, but not shown, cervical plate 500 could have prongs that grasp bone graft 502.

As one of ordinary skill in the art would recognize on reading this disclosure, the number of ways the bone grafts could be attached to the cervical plate is numerous. To the extent alternative attachment means are not expressly identify above, this description should not be limited to the embodiments identified and described above. Rather, the specific embodiments identified are for illustrative purposes.

Figure 6:
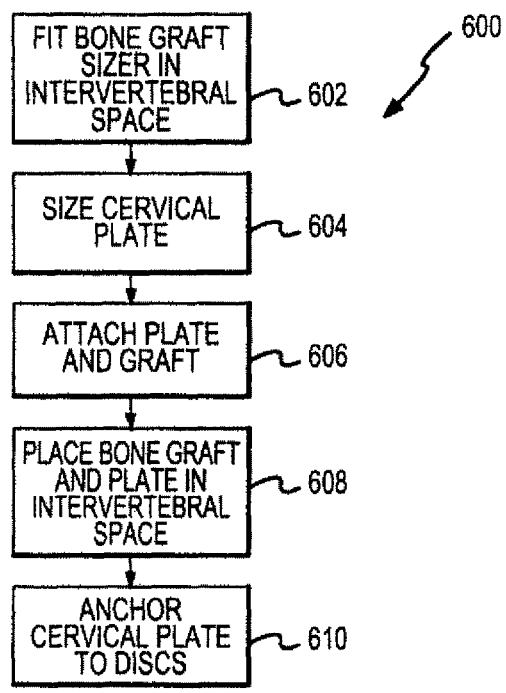
FIG. 6 is a flowchart 600 illustrating use of the present invention.

FIG. 6 is a flowchart 600 illustrating a method of using the present invention. In particular, the surgeon fits a bone graft into the intervertebral space, step 602. Then, with the bone graft in place and the adjacent discs holing the bone graft in place, the surgeon sizes a cervical plate, step 604. Once the cervical plate and bone graft are sized, the surgeon removes the plate and graft from the patient, and attaches the bone graft to the cervical plate, step 606. Next, the combination bone graft and plate device is placed in the intervertebral space such that the adjacent discs hold the bone graft and plate in place, step 608. The cervical plate is then anchored to the adjacent vertebral bodies, step 610. Because surgeon attached the cervical plate to the bone graft, and the adjacent vertebrae hold the bone graft in place, the cervical plate remains fixed in place while the surgeon anchors the plate to the vertebrae.

As one of ordinary skill in the art would recognize on reading the above disclosure, the same general device and procedure is used when inserting multiple bone grafts. For example, if fusing four vertebrae, a surgeon would need to place three bone grafts. Conventionally, the three bone grafts are sized and placed in the intervertebral space and a cervical plate is sized for the three grafts. Using the present invention, the three bone grafts could all be removed and attached to the cervical plate and then refitted into the patient. However, it is believed attaching multiple bone grafts to the cervical plate would make it difficult to fit the device into the patient. It is believed to be more efficient to insert bone grafts and size the bone grafts and cervical plate, then remove one of the bone grafts while leaving other bone grafts in the spine. The removed bone graft would be attached to the plate. The one bone graft with the cervical plate attached is refitted into the patient and screws can be used to anchor the entire device with the one bone graft providing the stability for the cervical plate.

As mentioned above, inserting the bone graft and cervical plate includes using a retracting device to hold the adjacent discs apart, inserting the bone grafts and sizing the cervical plate, removing cervical plate and the retracting device, allowing the adjacent discs to squeeze the bone graft, then replacing and anchoring the cervical plate. A difficulty arises using the present invention because the retracting devices need to be removed prior to placing and anchoring the cervical plate. Thus, when the bone graft is removed and attached to the cervical plate, the retracting devices need to be removed prior to replacing the combined bone graft and cervical plate. However, on removing the retracting devices, the adjacent discs move together making it difficult to insert the bone graft between the adjacent discs.

FIG. 7 shows an impactor 700 capable of opening the space between the discs to ease the insertion of the bone graft attached to the cervical plate. Impactor 700 has a handle 702, a cervical plate holder 704, and prongs 706 forming cavity 708. Impactor 702 could have various numbers of prongs, but it is believed two prongs work well. Cervical plate holder 704 is designed to hold the cervical plate such that the prongs 706 extend downward beyond the cervical plate and bone graft attachment. Prongs 706 could be spaced to form cavity 708 such that placing the cervical plate in the cavity 708 would form a friction fitting releasably coupling the cervical plate to the impactor 700. The prongs 706 would act as a wedge to separate the adjacent discs allowing placement of the bone graft in the intervertebral space. Once the bone graft is placed, the impactor 700 would be completely removed from the patient. Thus, the cervical plate and impactor would be releasably coupled prior to insertion. FIG. 8 shows a top side elevation view of the impactor 700 holding a cervical plate 802. Cervical plate 802 is shown without a viewing window, but one could be used if desired.

Figure 9:
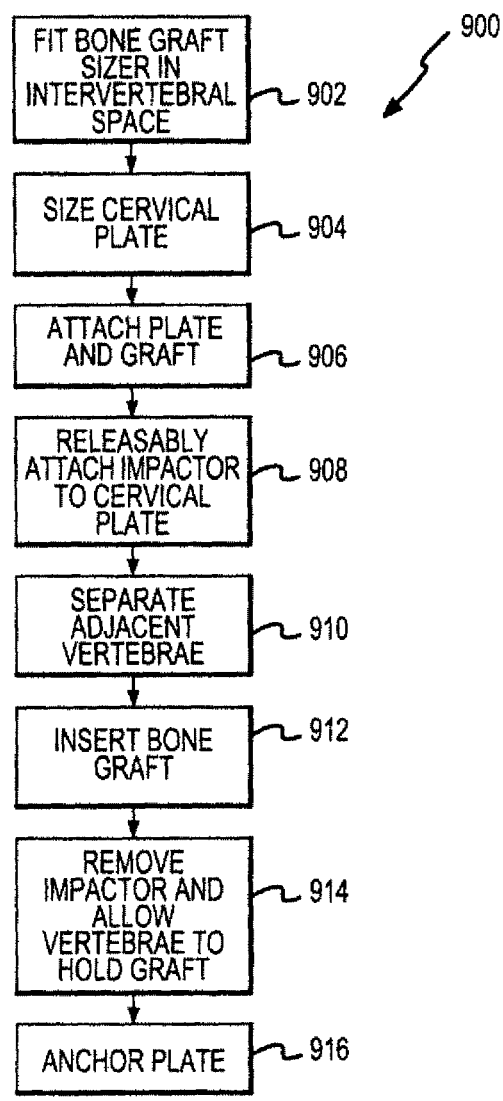
FIG. 9 is a flowchart illustrative of a use of the impactor consistent with the present invention.

FIG. 9 is a flowchart 900 illustrating using the impactor 700 with the cervical plate 802. For convenience, flowchart 900 is described for insertion of a single bone graft. One of skill in the art will recognize on reading the disclosure, however, that the device and procedure would be usable with insertion of multiple bone grafts. Initially, the surgeon fits a bone graft into the intervertebral space, step 902. Then, with the bone graft in place and the adjacent discs holing the bone graft in place, the surgeon sizes a cervical plate, step 904. Once the cervical plate and bone graft are sized, the surgeon removes the plate and graft from the patient, and attaches the bone graft and the cervical plate, step 906. Next, the impactor is releasably attached to the cervical plate, step 908. The impactor with the cervical plate and bone graft is used to separate the adjacent vertebrae, step 910. With the impactor holding the adjacent vertebrae apart, the bone graft is inserted in the intervertebral space such that the cervical plate is placed to be anchored to the adjacent vertebrae, step 912. The impactor is removed allowing the adjacent vertebrae to hold the bone graft and cervical plate in place, step 914. Finally, the cervical plate is anchored to the vertebrae, step 916.

Once surgically placed and anchored, cervical plate bone screws have a tendency to become loose, which is commonly referred to as backing out. Many devices have been devised to inhibit bone screws from backing out; however, none are particularly satisfactory.

Figure 10A:
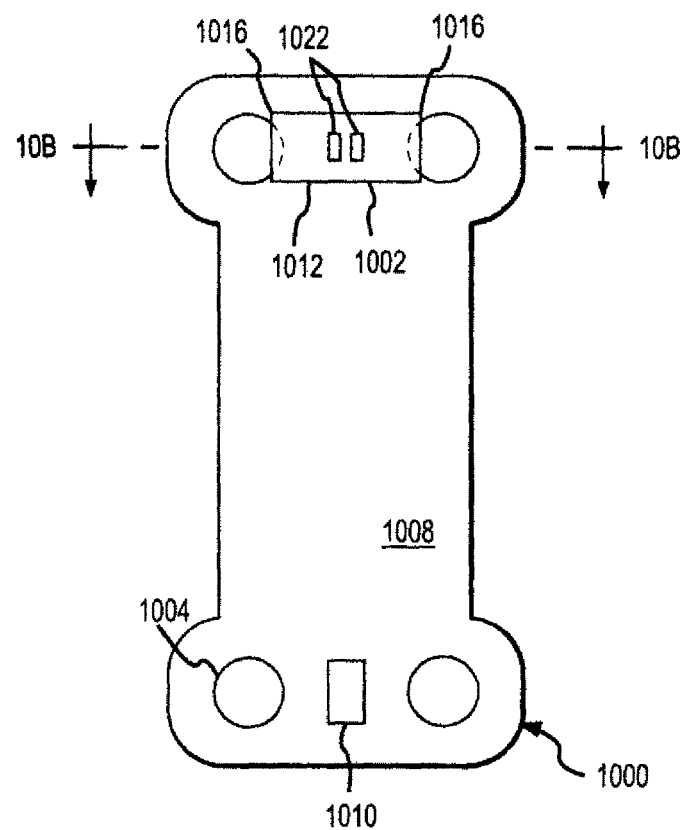
FIGS. 10A and 10B show an embodiment of a screw back out prevention device consistent with the present invention.
Figure 10B:
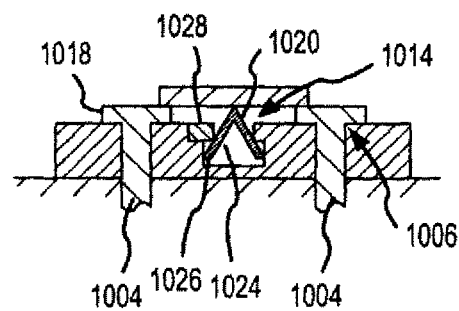

Referring now to FIGS. 10A and 10B, a cervical plate 1000 with a back out prevention device 1002 in accordance with one embodiment of the present invention is shown. While the respective vertebrae have not been specifically shown in FIGS. 10A and 10B, cervical plate 1000 has been surgically implanted, and bone screws 1004 have been threaded into vertebral bodies through screw holes 1006 in plate 1000. A surface 1008 of plate 1000 contains at least one channel 1010 or groove. Two grooves 1010 are shown, but channel 1010 could be a single channel extending the length of the plate as well. Back out prevention device 1002 comprises a cover 1012 and locking extension 1014 (best seen in FIG. 10B). Cover 1012 is sufficiently large to allow at least one perimeter edge 1016 of cover 1012 to extend over a head 1018 of screw 1004. When installed, edge 1016 is substantially aligned with head 1018 and prevents backing out of screw 1004. Locking extension 1014 comprises one or more elastic prongs 1020, for example biocompatible plastic or spring metal. Prongs 1020 fit into channel 1010 to hold back out prevention device 1002 in place. To facilitate placement of prongs 1020 into channel 1010, cover 1012 may have at least one access port 1022 through which a tool (not specifically shown) can be inserted. The tool would flex prong 1020 such that prong 1020 easily fits into channel 1010. When the tool is removed, prong 1020 would tend to return to its original position and apply a frictional force to seat back out prevention device. Similarly, the tool could compress prongs 1020 to allow removal of backout prevention device 1002 as desired.

As shown by FIG. 10B, one embodiment of back out prevention device 1002 comprises cover 1012 with multiple prongs 1020 forming an inverted V shape. While the inverted V shape is shown for convenience, prongs 1020 may be independent of each other and baised as explained below. Prongs 1020 have a distal end 1024 with a locking edge 1026. In this case, locking edge 1026 comprises a shoulder or protrusion. As shown in FIG. 10B, locking edge 1026 could have a wedge shape to facilitate insertion of prongs 1020 into channel 1010. In this case, use of the tool and access port 1022 may be unnecessary. Correspondingly, channel 1010 includes an engaging edge 1028. Prongs 1020 should be biased to force locking edge 1026 and engaging edge 1028. In this case, prongs 1020 are biased to diverge, but in other arrangements they may be biased to converge. In this case, engaging edge 1028 comprises a lip or undercut. Of course, locking edge 1026 could comprise a hollow and engaging edge 1028 could comprise a corresponding protrusion, etc. Similarly, surface 1008 could have a raised extension with protrusions and cover 1012 could have a channel with a lip or shoulder. The channel of cover 1012 would be aligned with raised extensions on surface 1008 forming a fitting, such as a snap lock or a frictional engagement.

While shown as a square or rectangular shape, cover 1012 can be formed of many shapes and/or configurations. For example, cover 1012 could be elliptical, circular, some other polygon, linear, an arc or curve, convex or concave, irregular, a zig-zag, a letter shape, or the like. Further, as shown head 1018 resides above plate 1000 and cover plate 1012 resides above head 1018; however, one of skill in the art would recognize on reading the disclosure, that head 1018 and cover plate 1012 could be countersunk such that the head 1018 and cover plate 1012 reside substantially in the same plane as plate 1000.

Figure 11:
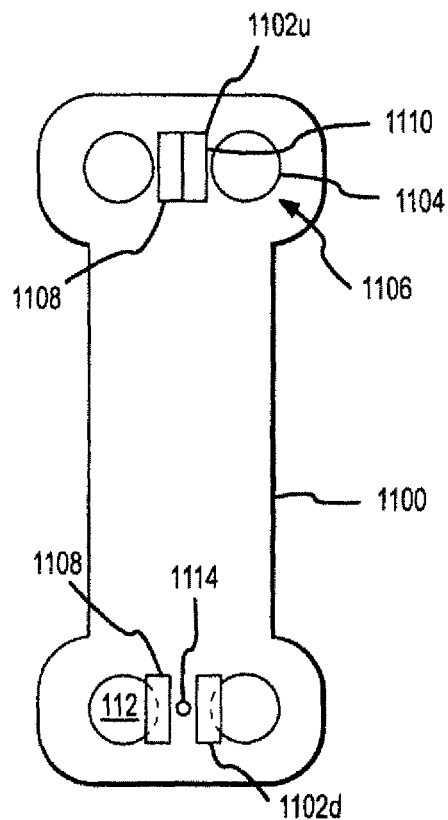
FIG. 11 shows another embodiment of a screw back out prevention device consistent with the present invention.

Referring now to FIG. 11, another cervical plate 1100 with two back out prevention devices 1102d and 1102u is shown. Prevention device 1102d is shown deployed and prevention device 1102u is shown undeployed. Plate 1100 would be surgically implanted and bone screws 1104 threaded into the vertebral body through screw holes 1106.

Prevention devices 1102 comprise a plurality of bars 1108 having a deployed state (shown by prevention device 1102d) and an undeployed state (shown by prevention device 1102u). In the deployed state, prevention device 1102d has a peripheral edge 1110 on bars 1108 that extend over a head 1112 of screws 1104. In the undeployed state, prevention device 1102u has bars 1108 relatively closer to each other where peripheral edge 1110 does not extend over head 1112, which makes screws 1104 freely movable. When deployed, a locking device 1114, such as a pin, stud, screw, clip, cam, or the like is inserted or rotated between bars 1108 to lock prevention device 1102d in the deployed state. For example, after bars 1108 are deployed, a screw could be inserted to maintain the separation. Alternatively, a cam could be rotated to maintain separation. Locking device 1114 would be removed to undeploy the prevention device. While prevention device 1102 is shown sized similar to a single screw head, prevention device 102 could have bars 1108 that extend the length of the cervical plate so only one prevention device is necessary for multiple sets of screws.

Figure 12:
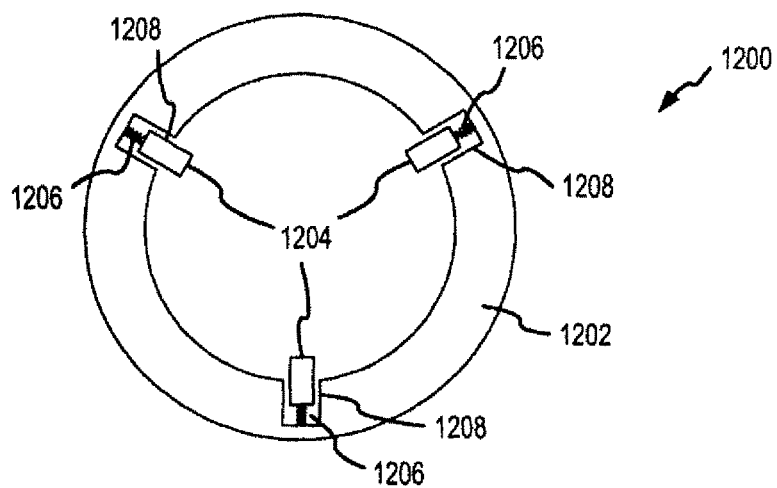
FIG. 12 shows another embodiment of a screw back out prevention device consistent with the present invention.

FIG. 12 shows a top plan view of another back out prevention device 1200 consistent with the present invention. Unlike prevention devices 1000 and 1100, which generally prevent screws from backing out by engaging a screw head, prevention device 1200 engages, for example, a thread of a screw or a notch located, for example, in the screw head. Back out prevention device 1200 includes a bushing 1202 and at least one locking pin 1204, in which three pins 1204 are shown in this case. Bushing 1202 forms a ring or thread through which a screw (not specifically shown) can be threaded. A spring 1206 or other elastic device pushes locking pin 1204 radially inward such that pins 1204 provide sufficient force on at least one thread or notch of the bone screws (not specifically shown in FIG. 12). Spring 1206 should not be construed as a conventional helical spring, but could be a number of elastic devices including, for example, elastic plastics, air loaded dampers, magnetics, shaped memory alloys, or the like. Thus, spring or spring loaded should be used generically to mean a device with elastic movement ability. Basically, spring 1206 needs to provide sufficient outward force to seat pin 1204 against a thread, notch, or surface of the screw or screw head, but be sufficiently resilient to allow the screw to be threaded into bone. (Notice, spring 1206 and pin 1204 could be combined into a single unit using). Spring 1206 could be flush between the pin 1204 and bushing or, as shown, spring 1206 could reside in a channel 1208 in bushing 1202.

Figure 13:
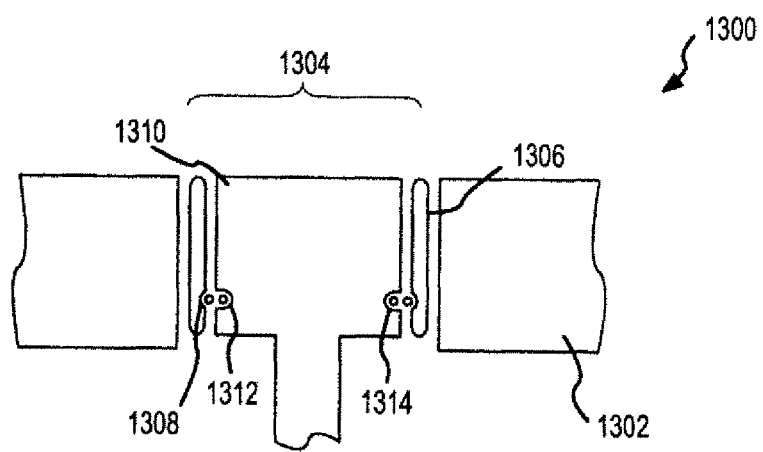
FIG. 13 shows still another embodiment of a screw back out prevention device consistent with the present invention.
Figure 14:
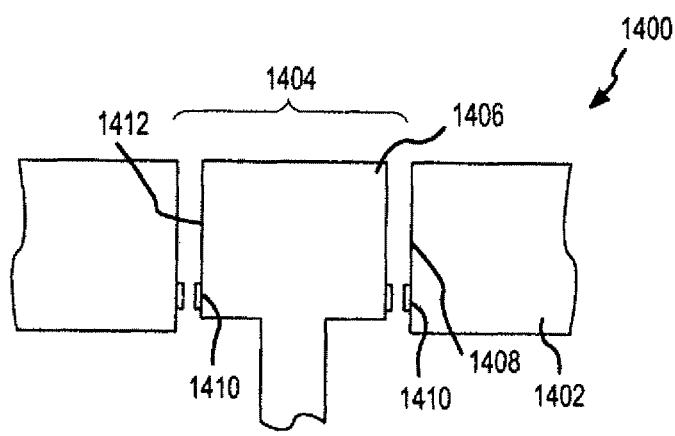
FIG. 14 shows still another embodiment of a screw back out prevention device consistent with the present invention.

FIGS. 13 and 14 show cross-sectional views of screw back out prevention device 1300 and 1400, respectively. FIG. 13 shows a portion of a cervical plate 1302 about a screw hole 1304. Residing in screw hole 1304 would be a bushing 1306 that contains a notch 1308, groove, or channel. A screw would be threaded into vertebral bodies (not specifically shown in FIG. 13) through screw hole 1304 such that screw head 1310 resides as shown. Screw head 1310 has a notch 1312, groove, or channel, corresponding to notch 1308. Residing in notch 1308 and notch 1312 is a self-bonding material 1314, such as high molecular weight polyethylene, nylons, and biopolymers and other self-bonding material commonly used in the aeronautical and automotive industries. Instead of self-bonding material 1314, material 1314 could be replaced with heat fusible material, pressure sensitive material, radiation curing, or other adhesives that require activation to adhere. Self-bonding material 1314 provides back out prevention because when the screw is threaded into the vertebral bodies bonding material 1314 in notch 1308 engages bonding material 1314 in notch 1312 and bonds. Thus, screw head 1310 is held in place. Although shown in a notch, material 1314 could be layered, such as by a coating or spray, on bushing 1306 and screw head 1310.

Similarly, FIG. 14 shows a portion of a cervical plate 1402 about a screw hole 1404. Residing in screw hole 1404 is a screw head 1406. Screw hole 1404 as sidewalls 1408. Residing on sidewalls 1408 exists at least one strip of self-bonding material 1410. While the materials identified above for material 1314 could be used, in this particular example, self-bonding material 1410 is a spray on type of material. Screw head 1406 has exterior sidewalls 1412. Residing on sidewalls 1412 exists at least one strip of self-bonding material 1410 corresponding to the strip of self-bonding material 1410 on sidewalls 1408. Again, instead of a spray or coating, material 1410 could reside in a notch on sidewall 1408 and sidewall 1412.

Alternatively to a self-bonding material, other materials may be used. For example material 1410 (or 1314) may be a type of heat fusion plastic. To use heat fusion, once the screw is threaded and the materials align, a heat activation signal would be applied to fuse the materials. Other bonding materials, such as epoxies, acrylics (such cyanoacrylates and anaerobics), silicones, pastes, tapes, and glues, and the like could be used for bonding material 1410 (or 1314), but would inhibit threading of the screw as well as be useful as a screw back out prevention device.

While the invention has been particularly shown and described with reference to some embodiment thereof, it will be understood by those skilled in the art that various other changes in the form and details may be made without departing from the spirit and scope of the invention.

We claim:

1. A back out prevention device in a cervical plate, the cervical plate comprising at least one through hole, the prevention device comprising:
   a bushing residing in the through hole;
   a screw; and
   at least one first bonding material, wherein
   the bushing has an inner sidewall containing a first groove therein, wherein the first groove has at least first and second portions that reside on opposing sides of the inner sidewall of the bushing and the at least one first bonding material residing in the first groove, wherein
   the screw comprises a screw head and a shank, wherein
   the screw head has an outer sidewall containing a second groove therein, wherein the second groove has at least first and second portions that reside on opposing sides of the outer sidewall and at least one second bonding material residing in the second groove, and the first and second portions of the first groove and the first and second portions of the second groove are configured to align coaxially with one another and form a space extending therebetween when the bushing and the screw head are configured in attachment with one another, such that
   when the screw is threaded into a vertebral body, the at least one first bonding material in the first groove of the inner sidewall aligns with the at least one second bonding material in the second groove of the outer sidewall to fill the space extending therebetween and to form a bond that inhibits the screw from backing out.

2. The screw back out prevention device according to claim 1, wherein the at least one first bonding material and the at least one second bonding material are self-bonding materials.

3. The screw back out prevention device according to claim 2, wherein the self bonding material is coated on the inner sidewall and the outer sidewall.

4. The screw back out prevention device according to claim 1, wherein the at least one first bonding material and the at least one second bonding material are at least one of a thermally activated bonding material, pressure activated bonding material, an electrically activated bonding material, and a radiation activated bonding material.

5. The screw back out prevention device according to claim 1, wherein the at least one first bonding material and the at least one second bonding material are different materials.

6. The screw back out prevention device according to claim 1, wherein the at least one first bonding material and the at least one second bonding material are at least one of an epoxy, an acrylics, a resin, a silicone, an adhesive, a glue, and a tape.

7. A back out prevention device in a cervical plate, the cervical plate comprising at least one through hole, the prevention device comprising:
   a bushing residing in the through hole, the bushing comprising a bore;
   a screw;
   the bushing has an inner sidewall containing a first groove that has opposing portions that are coaxially aligned on opposite sides of the bushing and a first bonding material residing in the first groove;
   the screw comprises a screw head containing a second groove that has opposing portions that are coaxially aligned on opposite sides of the screw head and a shank and a second bonding material residing in the second groove, and the opposing portions of the first groove are coaxially aligned with the opposing portions of the second groove when the bushing and the screw head are configured in attachment with one another; such that
   when the screw is threaded into a vertebral body, the first bonding material in the first groove substantially aligns with the second bonding material in the second groove of the screw head forming a bond that inhibits the screw from backing out.

* * * * *